(12) United States Patent
Bollenbach et al.

(10) Patent No.: US 8,672,901 B2
(45) Date of Patent: Mar. 18, 2014

(54) PRODUCT CONTAINER HOLDER FOR AN INJECTION DEVICE AND FOR RECEIVING A PRODUCT CONTAINER

(75) Inventors: Markus Bollenbach, Bern (CH); Ursina Streit, Schönbühl (CH); Daniel Kuenzli, Muri (CH); Nadine Kaufmann, Burgdorf (CH); Ulrich Moser, Heimiswil (CH)

(73) Assignee: TecPharma Licensing AG, Burgdorf (CH)

( * ) Notice: Subject to any disclaimer, the term of this patent is extended or adjusted under 35 U.S.C. 154(b) by 23 days.

(21) Appl. No.: 13/217,741

(22) Filed: Aug. 25, 2011

(65) Prior Publication Data

US 2012/0053528 A1    Mar. 1, 2012

Related U.S. Application Data

(63) Continuation of application No. PCT/EP2009/052323, filed on Feb. 26, 2009.

(30) Foreign Application Priority Data

Feb. 26, 2009   (WO) ................. PCT/EP2009/052323

(51) Int. Cl.
   *A61M 5/00*   (2006.01)
   *A61M 5/32*   (2006.01)

(52) U.S. Cl.
   USPC .......................................... 604/234; 604/197

(58) Field of Classification Search
   USPC .................. 604/181, 197, 187, 218, 232, 234
   See application file for complete search history.

(56) References Cited

U.S. PATENT DOCUMENTS

| | | | | |
|---|---|---|---|---|
| 3,144,178 | A * | 8/1964 | Sarnoff ......................... | 222/327 |
| 4,231,368 | A | 11/1980 | Becker | |
| 4,787,891 | A * | 11/1988 | Levin et al. ................... | 604/136 |
| 5,002,537 | A * | 3/1991 | Hoffman et al. .............. | 604/232 |
| 5,078,698 | A * | 1/1992 | Stiehl et al. ................... | 604/235 |
| 5,514,097 | A * | 5/1996 | Knauer .......................... | 604/136 |
| 5,879,336 | A * | 3/1999 | Brinon .......................... | 604/191 |
| 6,544,234 | B1 | 4/2003 | Gabriel | |
| 6,692,469 | B1 | 2/2004 | Weeks et al. | |
| 7,118,552 | B2 * | 10/2006 | Shaw et al. ................... | 604/110 |

(Continued)

FOREIGN PATENT DOCUMENTS

| | | |
|---|---|---|
| DE | 10 2007 013 836 | 9/2008 |
| GB | 2434317 | 7/2007 |

(Continued)

*Primary Examiner* — Emily Schmidt
*Assistant Examiner* — William Carpenter
(74) *Attorney, Agent, or Firm* — Dorsey & Whitney LLP; Stuart R. Hemphill, Esq.

(57) ABSTRACT

A product container holder for accommodating a product container, wherein the product container holder can be separately handled and can be inserted into an injection device, and includes an engaging member that can be moved transversely to the longitudinal axis of the product container holder and which can block a movement of the product container relative to the product container holder in the distal direction, and a securing structure which can be moved relative to the engaging member from an initial position to a securing position in which it restricts the mobility of the engaging member. In some embodiments, a method of making and a method of using the product container holder is encompassed, as is a container and an injection device with which the holder can be used.

11 Claims, 5 Drawing Sheets

(56) References Cited

U.S. PATENT DOCUMENTS

| | | | |
|---|---|---|---|
| 7,175,055 B2 * | 2/2007 | Hansen et al. | 222/326 |
| 7,500,963 B2 * | 3/2009 | Westbye et al. | 604/192 |
| 8,298,194 B2 * | 10/2012 | Moller | 604/207 |
| 8,313,465 B2 * | 11/2012 | Harrison | 604/136 |
| 2004/0116859 A1 * | 6/2004 | Alchas et al. | 604/117 |
| 2004/0134563 A1 * | 7/2004 | Rice et al. | 141/329 |
| 2004/0225262 A1 * | 11/2004 | Fathallah et al. | 604/198 |
| 2005/0020979 A1 | 1/2005 | Westbye et al. | |
| 2005/0101919 A1 | 5/2005 | Brunnberg | |
| 2005/0277896 A1 * | 12/2005 | Messerli et al. | 604/240 |
| 2007/0173770 A1 * | 7/2007 | Stamp | 604/187 |
| 2008/0262438 A1 * | 10/2008 | Bollenbach et al. | 604/207 |
| 2010/0137801 A1 | 6/2010 | Streit et al. | |
| 2011/0152822 A1 * | 6/2011 | Drunk et al. | 604/415 |
| 2011/0230827 A1 * | 9/2011 | Mori et al. | 604/82 |

FOREIGN PATENT DOCUMENTS

| | | |
|---|---|---|
| GB | 2438591 | 12/2007 |
| WO | 94/11041 | 5/1994 |
| WO | 00/24441 | 5/2000 |
| WO | 2005/097252 | 10/2005 |
| WO | 2005/115507 | 12/2005 |
| WO | 2006/106295 | 10/2006 |

* cited by examiner

PRODUCT CONTAINER HOLDER FOR AN INJECTION DEVICE AND FOR RECEIVING A PRODUCT CONTAINER

CROSS-REFERENCE TO RELATED APPLICATIONS

This application is a Continuation of International Patent Application No. PCT/EP2009/052323 filed Feb. 26, 2009, the contents of which are hereby incorporated by reference.

BACKGROUND

The present invention relates to devices for injecting, delivering, infusing, dispensing or administering a substance or product, and to methods of making and using such devices. More particularly, it relates to containers for containing a substance or product to be injected or delivered to a patient, and to a product container holder for a container and for an injection device for administering a liquid product, e.g. a liquid drug. The invention also relates to a sub-assembly comprising a product container and a product container holder, and to a method for assembling an injection device, e.g. an auto-injection device or auto-injector.

Injection apparatus or devices, including so-called automatice injectors or auto-injectors, are known from the prior art. In the case of auto-injectors, a product or substance to be administered is automatically administered after the auto-injector is triggered, i.e. a needle is automatically injected into a patient's tissue and the product is then automatically delivered. In some auto-injectors, the needle is automatically retracted into the auto-injector after a product delivery is complete. In other auto-injectors, the needle is manually removed from the injection point.

In the case of auto-injectors, a product container containing the product to be administered is often accommodated in a product container holder. The accommodated product containers can be so-called standard syringes, or an ampoule, vial or reservoir, which are often made of glass. To reduce the complexity of approval proceedings for product containers, standard syringes which have already been approved may be built into or used with injection devices or auto-injectors. Standard syringes can comprise a flange at their distal end, i.e. the end opposite the needle, which is also referred to as a finger flange because it forms an abutment for the middle and index finger when manually administering the contents of the syringe. Simultaneously using the flange to fasten the product container to a product container holder is known from the prior art, as described for example in DE 10 2007 013 836 A1 (and its equivalent US Publication 2010/0137801). Quite large forces and/or momenta are exerted on the syringe flange when advancing the product container to inject the needle and deliver the product. In certain circumstances, this can cause the syringe flange to break after the injection device is triggered, making it no longer possible to properly administer the product.

Because injection devices, including auto-injectors, are mass-produced, they are assembled mechanically. In addition to high safety and reliability requirements, demands are also therefore made on the parts of the injection device with respect to their handling and/or ability to be mechanically processed, e.g. formed and/or assembled.

SUMMARY

An object of the present invention is to provide a product container holder for accommodating a product container which protects the product container from damage during administering and which can be easily assembled. It is also an object of the present invention to provide a sub-assembly consisting of a product container holder and a product container, in which the product container is protected from damage during administering and which can be easily assembled. It is another object of the present invention to provide a method for safely and conveniently assembling an injection device, including using a product or medicinal substance container in a product container holder.

In one embodiment, the present invention comprises a product container holder for accommodating a product container, wherein the product container holder can be separately handled and can be inserted into an injection device, and comprises an engaging member for engaging the product container such that the engaging member can be moved transversely to the longitudinal axis (L) of the product container holder and can block or prevent a movement of the product container relative to the product container holder in the distal direction, and a securing structure or lock which can be moved relative to the engaging member from an initial position to a securing position in which it restricts and/or prevents the movement of the engaging member.

In one embodiment, the invention involves a product container holder for accommodating a product container, wherein the product container holder is a unit which can be separately handled and can be inserted into an injection device to administer a product. When the product container is inserted into the product container holder, the product container holder surrounds at least some, e.g. most or all of the product container. The product container holder forms a firm seating for the product container. The product container can thus be shifted together with the product container holder as a unit in the injection device, for example to perform an injection movement of a needle arranged on the product container, wherein the product container is fixed relative to the product container holder, while the product container holder can be moved relative to the injection device, such as relative to a housing or another portion of the device. In some embodiments, a method of making and a method of using the product container holder is encompassed, as is a container and an injection device with which the holder can be used.

A product container in accordance with the present invention can be individually adapted or unique, but in some preferred embodiments, it may be a standard product container. The product container can, for example, be an ampoule or carpoule, the front end of which can have a needle attached to it and is sealed by a pierceable septum. The needle can be fastened, for example releasably, to the product container by a Luer coupling or other suitable connection or connective method.

In some preferred embodiments, the product container is a so-called syringe which, like a carpoule or ampoule, comprises a storage portion for the product. The storage portion may be cylindrical. The storage portion is tapered at its distal end, such that it forms a collar, and is sealed except for a small opening for delivering the product. The product or substance to be administered is situated proximally with respect to the distal seal of the storage portion and is distally closed off by a piston which abuts the cylindrical storage portion, forming a seal. The piston can be shifted in the distal direction to deliver the product, whereby the product is forced out of the storage portion. A needle can be releasably attached, for example screwed, to the syringe or, as in some preferred embodiments, the needle is fixedly, i.e. non-releasably, connected to the syringe. The needle is fluidically connected to the product, such that when the piston is shifted in the distal direction, the product is dispensed through the needle. The product container, e.g. the syringe, comprises a flange, which can also be referred to as a finger flange, at its proximal end. When the product container is inserted completely into the product container holder, the flange can be in abutment with the product container holder. However, in some preferred embodiments, the product container does not enter into abutment with the product container holder when it is inserted completely into the product container holder, thereby reliably avoiding damage due to injection forces and delivery forces which may act on the product container during administering.

In some embodiments, the product container holder can be thought of and/or referred to as a unit which can be separately handled because it can be handled as a single piece comprising its parts and, in some embodiments, with features of the injection device with which it to be used, e.g. features or structures within and/or outside the injection device. The parts of the product container holder can remain coherent by themselves in or outside the injection device. The product container holder can be formed in one or more parts; in some preferred embodiments, it consists of one part at least in its original state, e.g. before it is assembled. In its end state, e.g. after it has been completely assembled, it can consist of two or more parts joined to make a single unit. Because the product container holder is a unit which can be separately handled, it can be very easily assembled.

In one preferred embodiment, an injection device for administering the product is an auto-injector or auto-injection device. In some preferred embodiments, after the injection device has been triggered, a needle is automatically injected and the product automatically dispensed via the needle. Optionally, the needle can be automatically retracted after the injection. Such a device is described in DE 10 2007 013 836 A1 (and its equivalent US Publication 2010/0137801), the disclosure and teaching of which, including with regard to its injection, delivery and retraction mechanism and with regard to its movement sequence, are incorporated herein by reference.

In some embodiments, the product container holder exhibits a longitudinal axis which usually corresponds to the longitudinal axis of the product container and the longitudinal axis of the needle. In some preferred embodiments, the longitudinal axis can also correspond to the longitudinal axis of the injection device.

In some embodiments, the product container holder comprises an engaging member for the product container which is arranged such that it can be moved transversely relative to the longitudinal axis of the product container holder. The movement of the product container relative to the product container holder in the distal direction can be blocked or prevented by the engaging member. The movement of the engaging member transverse to the longitudinal axis can be a linear movement or a pivoting movement. The mode of operation of the engaging member can be based on a positive fit and/or a force fit, e.g. a frictional fit. The engaging member can expediently be moved into engagement with the product container. The engaging member can, for example, engage in a positive fit with a collar which is formed on the outer side of the product container and distally with respect to the storage portion, wherein the engaging member forms a reaction surface which can absorb a force acting on the product container in the distal direction and divert it into the product container holder. In this case, the engaging member forms a firm seat or fit for the product container, such that it is prevented from moving in the distal direction relative to the product container holder. A positive-fit engaging member can, for example, be formed as a cam which protrudes inwardly.

In another embodiment, the engaging member can act on the storage portion of a product container, for example laterally or on the cylindrical outer surface of the storage portion, and clamp the product container. Such an engagement can be referred to as a force-fit engagement, because the connection is based on a frictional fit. Due to the frictional fit, it is not possible to shift the product container in the distal direction. A force which acts on the product container in the distal direction can diverted via the frictional fit onto the engaging member and from the engaging member onto the product container holder.

In yet another embodiment, at least one recess can be provided on the storage portion, e.g. on its cylindrical outer surface, and the engaging member can engage with said recess, such that a predominantly positive-fit engagement is formed which depending on the configuration of the at least one recess can also have a force-fit and/or frictional-fit active component.

In accordance with some embodiments, the product container holder comprises a lock or securing means which can be moved relative to the engaging member from an initial position into a securing position. In the securing position, the securing means secures the engagement of the engaging member by restricting the mobility of the engaging member. The mobility of the engaging member is restricted such that it can no longer be moved out of engagement with the product container. The securing means can also serve to tense the engaging member in its engagement with the product container. In some embodiments, the securing means blocks, or locks, stops or prevents, the mobility or movement of the engaging member transverse to and at least away from the longitudinal axis of the product container holder, i.e. such that the engaging member can only be moved away from the longitudinal axis of the product container holder by destroying or at least manipulating the securing means. Thus, the product container is securely accommodated in the product container holder.

In some embodiments, in the initial position of the securing means, the engaging member can be moved into and out of engagement with the product container. The movement can be achieved manually, by a gear or, in some preferred embodiments by a spring-elastically arranged engaging member. The spring force can, for example, press the engaging member in the direction of its engagement with the product container.

When the product container is inserted into the product container holder via a proximal opening of the product container holder, as in some preferred embodiments, the engaging means can pass into engagement with the product container, for example latch onto it or act on it, when the product container has been completely inserted. The spring-elastically mounted engaging member can also permit a product container to be inserted which exhibits a greater diameter at its distal end than at the storage portion and also at the point at which the engaging means is properly supposed to enter into engagement with the product container. Such a portion exhibiting a greater diameter can be formed by a needle protecting cap which can be made of rubber or a hard plastic or a combination of these. In a dispatched or shipped product container filled with product, the needle protecting cap may be already arranged on the product container and/or protectively over the needle to preserve the sterility of the needle. Typically, the needle must not or cannot be removed to assemble the injection device, because the needle would no longer be sterile. Embodiments of the present invention allow the product container together with the needle protecting cap to be inserted into the product container holder.

In the initial position, the securing means or lock permits the movement of the engaging member, while in the securing position, it no longer permits or at least restricts the movement of the engaging member. The securing means is expediently situated in the initial position as the product container is inserted and is then moved into the securing position, such that the product container is at least blocked or stopped against moving in the distal direction.

In some preferred embodiments, the engaging member can be moved flexibly, i.e. the engaging member can itself be flexible or can be flexibly mounted.

In some preferred embodiments, the product container holder can comprise at least one guiding member, in some preferred embodiments two, three or even more guiding members, which can laterally guide the product container. The inserted product container is laterally guided by the at least one guiding member such that it has nearly no or only very little lateral clearance. The at least one guiding member can be elastically or spring-elastically pliable or can be elastically and/or spring-elastically arranged, wherein the engaging member can be arranged on or carried by the at least one guiding member. One engaging member can be provided for each guiding member. The guiding member or members can exhibit an elongated shape, wherein the guiding members can be connected to each other, e.g. forming one piece, at their proximal ends. An element which is annular in cross-section can connect the guiding members to each other. The guiding members can thus be formed as one piece.

Alternatively or additionally, the product container holder can comprise a number of guiding members which are separate from each other and distributed over a circumference. The guiding members can either be elastic in their own right or can be mounted, elastically or in a joint, at their fastening points by the structure or element which connects the guiding members to each other. In some preferred embodiments, two guiding members are provided which are arranged oppositely on the circumference, wherein a cavity is formed between the two guiding members, through which it is possible to see into the interior of the product container holder and, when a product container is inserted, to see the product or substance therein. The cavity can approximately exhibit an axial length by which the piston can be shifted within the product container.

In some embodiments, the securing means can surround the engaging member and form a passage for the engaging member and/or the product container. The engaging member can be arranged between the product container and the securing means when the securing means is situated in the securing position. The securing means can be an element which is annular in cross-section and surrounds the product container and the engaging member or members. A securing means configured as a ring can exhibit a length, as measured along the longitudinal axis, which is smaller than the diameter of the ring. In some preferred embodiments, the length of the ring as measured along the longitudinal direction may be at most four times as large as the diameter of the ring. The ring generally may be dimensioned such that the product container is still visible through the cavity between the guiding members when the ring is situated in its securing position. It can therefore generally be said that the securing means is axially dimensioned such that when a product container is inserted, the contents of the product container are for the most part completely visible. Alternatively or additionally, the securing means can be configured such that in the securing position, its proximal end at most overlaps the piston of the product container which has been completely emptied by product delivery. The remaining volume of the product container situated proximally behind the piston is thus still visible to the user.

Alternatively or additionally, the securing means—e.g. the ring—can substantially be inflexible, i.e. can be significantly less flexible than the arrangement of the engaging members or the engaging member.

In its securing position, the securing means can be arranged by a connector, connective structure or connecting means such that it cannot be shifted relative to the engaging member along the longitudinal axis. The securing means is blocked or locked against moving along the longitudinal axis in the securing position, and/or also blocked against rotating relative to the product container holder and/or the at least one engaging member or the at least one guiding member. It is thus possible to ensure that the securing means cannot inadvertently be moved out of the securing position. The connecting means is based on a positive fit and/or force fit. The securing means can be clamped in the securing position, wherein the connection is then a force-fit connection. The connecting means may be a latching connection or snap connection. To this end, one of the securing means and the engaging and/or guiding member can comprise a cavity, and the other of the securing means and the engaging and/or guiding member can comprise a cam, wherein the cam and the cavity interlock with each other in a securing position and thus form a positive-fit connection. In some preferred embodiments, the connective structure or connecting means, as measured along the longitudinal axis, is attached in the region of the engaging member. In some preferred embodiments, the securing means is arranged in the region of the engaging member and/or over the engaging member, provided it is situated in the securing position. The part of the connecting means which is formed by the securing means can be situated approximately in the middle between the distal and proximal end of the securing means.

In some preferred embodiments, the product container holder exhibits an overall length which is greater in the initial position than in the securing position of the securing means. In the securing position, the product container holder can—but need not—be shortened by about the axial length of the securing means. Alternatively or additionally, the securing means can form the distal end of the product container holder in its initial position. The securing means can be arranged distally with respect to the engaging member and/or the at least one guiding member, e.g. arranged at the distal end of the at least one guiding member.

In some preferred embodiments, the securing structure or securing means can be formed in a force fit, positive fit or material fit on the product container holder, e.g. on a guiding member, in its initial position in which it is arranged in relation to the engaging member such that the engaging member can be moved flexibly. The securing means can be in a clamping connection in its initial position, such that it is arranged in a force fit on the product container holder. The securing means can be arranged on the product container holder by a force connection or snap connection, wherein this is then a positive-fit connection. The securing means can be glued or fused to the product container holder or formed in one piece with the product container holder in its initial position, such that the securing means is arranged in a material fit on the product container holder in its initial position. In some preferred embodiments, an initial application of force is required to move the securing means out of its initial position, wherein said application of force releases the connection between the securing means and the product container holder. Advantageously, this ensures that in its initial position, the securing means is not detached from the product container holder and/or remains correctly positioned when the product container holder is handled as a unit which can be separately handled. This significantly facilitates the ability of the product container holder to be processed and/or assembled. It is thus only possible to release the connection, by applying a sufficiently large force between the securing means and the product container holder, when this is also in fact desired.

In one preferred embodiment, the securing means can be fastened to the remaining product container holder, e.g. to at least one guiding member, via at least one stay, wherein the stay serves as a predetermined breaking point and can be broken as the securing means moves into the securing position or out of the initial position. The stay or stays are another example of a material-fit connection which holds the securing means in its initial position. A number of stays can be provided, such as two or three stays for each guiding member, which connect the guiding members to the securing means. It is, of course, also possible to connect them using one stay for each guiding member.

In some preferred embodiments, the product container holder, i.e. also including the securing means, is manufactured in one piece using an injection-molding method. This embodiment is advantageous because the securing means is already correctly positioned with respect to the remaining product container holder as it is manufactured in the injection-molding machine. This reduces the effort of assembly and the costs, because only one part has to be handled, not several.

In some preferred embodiments, the described product container holder forms a sub-assembly with a product container, e.g. with the syringe. In some preferred embodiments, the engaging member is arranged along the longitudinal axis such that it acts on the product container, e.g. on the collar which is formed by the product container distally with respect to the storage portion in which the piston is guided, wherein it is advantageous if the axial position of the engaging member is selected such that the flange of the product container remains free of contact with the product container holder.

In some preferred embodiments, the product container comprises a needle which is covered by a needle protecting cap, wherein the engaging member is arranged along the longitudinal axis at a position such that it engages with a region between the needle protecting cap and the storage portion, and the flange at the end of the product container nonetheless remains free of contact with the product container holder.

The present invention also relates to methods for assembling an injection device, e.g. an auto-injector. In one embodiment, the method comprises the following steps:
  providing a product container, e.g. a syringe, which comprises a storage portion for accommodating a drug, a needle at one end of the storage portion, and a piston which can be axially moved in the storage portion;
  providing a product container holder, e.g. one such as has been described herein, which comprises an engaging member for the product container;
  combining the product container and the product container holder, wherein an engaging member which is arranged such that it can be moved transverse to the longitudinal axis of the product container holder, e.g. flexibly, acts on the product container such that a movement of the product container relative to the product container holder in the distal direction is blocked or prevented, wherein a lock or securing means is moved relative to the engaging member into a securing position in which it secures the engagement of the engaging member by restricting the flexible mobility of the engaging member.

In one preferred embodiment, the product container is first inserted into the product container holder and the securing means moved into the securing position, and the combination of the product container and the product container holder thus formed is then inserted into a first sub-assembly which comprises a front housing, e.g. a triggering element for the injection device and a removal cap which is adapted to the triggering element. In an auto-injector, the triggering element serves to be placed onto the injection point, wherein administering can be triggered by pressing the triggering element onto the injection point. It is advantageously possible to ensure that the product container can be combined with the product container holder outside the first sub-assembly and secured by the securing means.

In another preferred embodiment, the product container holder is first inserted into the first sub-assembly, and the product container is then inserted into the product container holder and the securing means moved into the securing position. The securing means is supported on the front housing and/or the triggering element or on the removal cap. As the product container is inserted, a force is exerted between the securing means and the remaining product container holder, e.g. by exerting a force on the flange, which is large enough that the force-fit, positive-fit or material-fit connection between the product container holder and the securing means is released, such that the remaining product container holder can be moved together with the product container relative to the triggering element, the removal cap and/or the securing means, until the securing means has assumed the securing position on the product container holder.

In some preferred embodiments, a predetermined breaking point between the securing means and the product container holder is released as the securing means moves into the securing position.

In another preferred embodiment, the triggering element and the product container holder are positioned with respect to each other, e.g. rotationally and/or translationally, such that a viewing window which is a cavity of the triggering element and a viewing window which is a cavity of the product container holder expose the product container to view. If the first sub-assembly is surrounded by a housing when it is inserted into an injection apparatus, the housing of the injection device also comprises a cavity or window which is positioned with respect to the viewing windows of the triggering element and the product container holder, e.g. rotationally and translationally, such that the product container is exposed to view.

In some preferred embodiment, a second sub-assembly is provided which contains the drive mechanism of the injection device and is connected to the first sub-assembly which has been combined with the product container and the product container holder. The first sub-assembly is inserted into the injection device via an opening at the distal end of a cylindrical housing of the injection device. The first sub-assembly then latches together with elements in the injection device.

DETAILED DESCRIPTION

With regard to fastening, mounting, attaching or connecting components of the present invention, unless specifically described as otherwise, suitable mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1A:
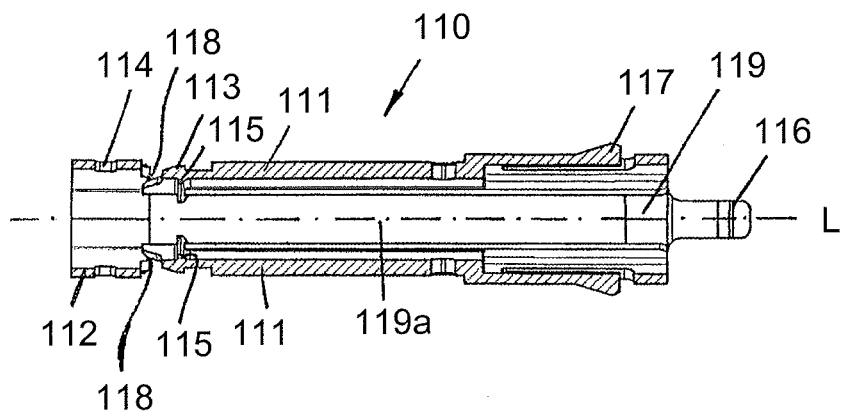
FIG. 1a is a sectional representation of one embodiment of a product container holder in accordance with the present invention, with an embodiment of a securing element in its initial position.
Figure 1B:
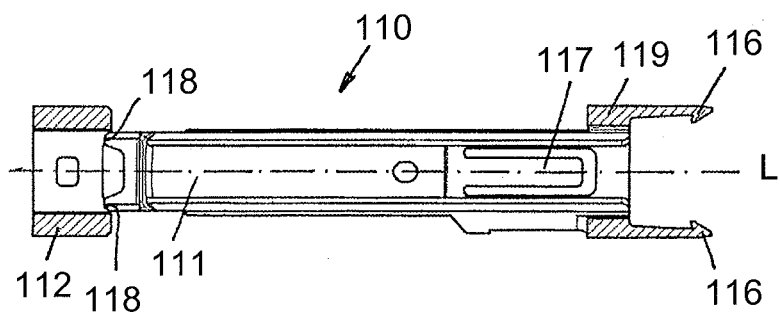
FIG. 1b depicts the product container holder from FIG. 1a, in a sectional representation rotated by 90° about the longitudinal axis.
Figure 1C:
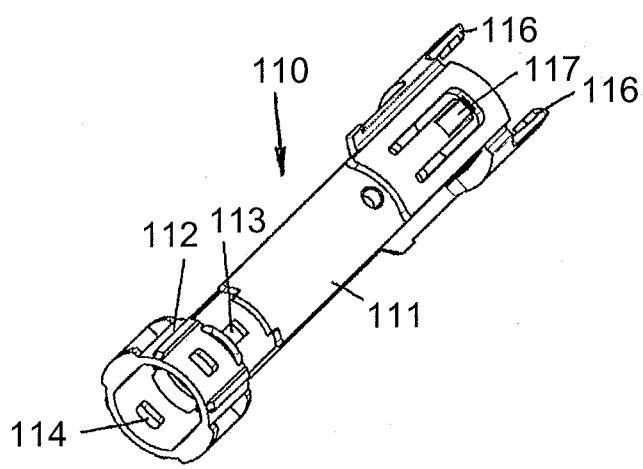
FIG. 1c depicts the product container holder from FIG. 1a, in a three-dimensional view.

All the figures, in particular FIGS. 1a, 1b and 1c, show a product container holder 110 which is manufactured in one part using an injection-molding method. The product container holder 110 is molded from a suitable plastic and comprises a connector 119 or base 119 which is annular in cross-section and provides sufficient space to enable a product container to be inserted into the product container holder 110 via the proximal end. Two fastening members 116 are arranged on the base 119 which extend in the proximal direction and are configured at the end in the shape of a hook. When the product container holder 110 is assembled into an injection device, the fastening members 116 can for example be connected to a functional sleeve which can shift the product container holder 110 in the completely assembled injection device in the distal direction to inject a needle and can also retract it again once the product has been completely administered. A suitable functional sleeve and an auto-injection apparatus which is equally suitable for the invention are described in DE 10 2007 013 836 A1 (and its equivalent US Publication 2010/0137801). The present invention can in fact be integrated with the injection device shown in DE 10 2007 013 836 A1 (and its equivalent US Publication 2010/0137801), in which the functional sleeve is indicated by the reference numeral 8.

Two guiding members 111 which are arranged oppositely on the circumference extend from the base 119 in the distal direction. The guiding members 111 serve on the one hand to laterally enclose and/or guide the product container 120 which can be inserted into the product container holder 110, such that there is relatively little clearance between the product container 120 and the guiding members 111. The product container 120 can best be seen in FIGS. 4a, 4b, 5a and 5b.

The product container holder 110, e.g. the guiding members 111, also form switching cams 117 which are spring-elastically arranged on an arm and project from the circumference of the product container holder 110. The switching cams 117 form part of a mechanism for retracting the product container holder 110 after the product has been completely administered. The function of the switching cams 117 is described in DE 10 2007 013 836 A1 (and its equivalent US Publication 2010/0137801), in which said function is indicated by the reference sign 17.

The guiding means 111 also comprise one or more engaging members 115 each, which protrude radially inwardly on the inner surface of the guiding members 111 which points and/or extends toward the longitudinal axis L. The engaging members 115 engage in a positive fit with a collar 122 of the product container 120 (FIG. 4a) to form a reaction surface which prevents the product container 120 from being able to be shifted relative to the product container holder 110 in the distal direction when the engaging members 115 engage with the collar 122. The reaction surface of the engaging members 115 which points in the proximal direction is correspondingly adapted to the inclination of the collar 122. A force which is exerted on the product container 120 in the distal direction can thus be diverted onto the product container holder 110 via the collar 122 and the engaging members 115 instead of via the flange 124.

The distal end of the product container holder 110 is formed by a securing structure, lock or securing means 112 which exhibits an annular cross-section and is respectively connected to the guiding means 111 by at least one stay 118. The stays 118 are likewise manufactured when the product container holder 110 is manufactured in the injection-molding method. This allows the product container holder 110 to be easy to handle because all of its parts are already positioned with respect to each other when it is expelled from the injection-molding tool.

The product container holder 110 comprises cams 113 which are arranged approximately in the region of the engaging members 115 as measured along the longitudinal axis L. The cams 113 are formed by the guiding members 111 and project radially outwardly. The cams 113 serve to engage with cavities 114 which are formed on the securing means 112.

Figure 4A:
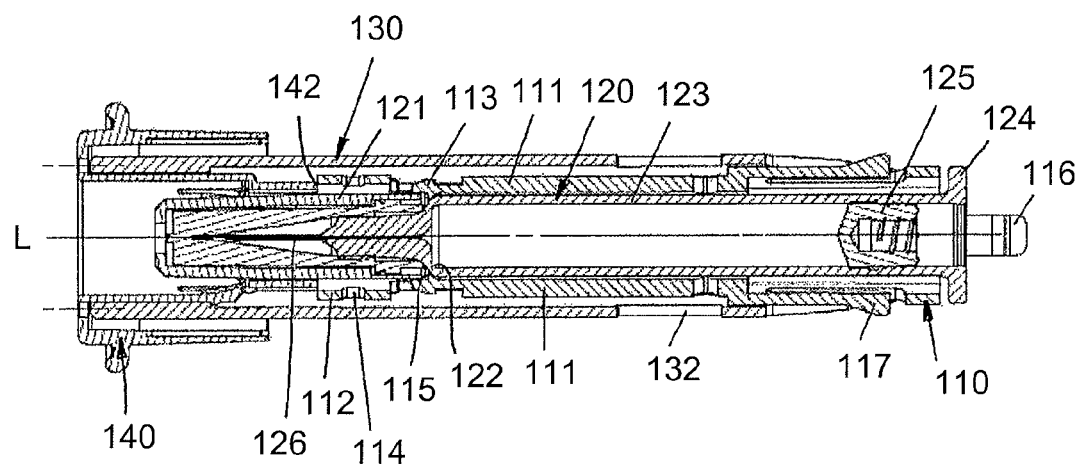
FIG. 4a is a sectional representation of the parts from FIG. 3a when combined, and a securing member in its initial position.
Figure 4B:
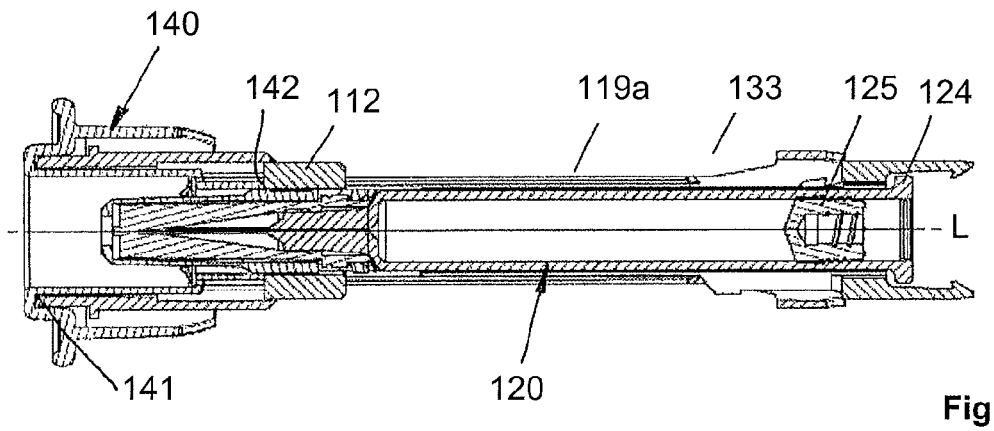
FIG. 4b depicts the combined parts from FIG. 4a, in a sectional representation rotated by 90° about the longitudinal axis.

As can be seen for example in FIGS. 4a and 4b, the product container comprises a needle protecting sleeve 121 which exhibits a larger outer diameter than the storage portion 123 of the product container 120.

When the product container 120 is inserted into the product container holder 110, the needle protecting cap 121 is moved past the engaging members 115. The engaging members 115 are moved transverse to the longitudinal axis L of the product container 120 such that the cross-section formed by the engaging members 115 is widened, such that the needle protecting cap 121 can pass the engaging members 115. As soon as the needle protecting cap 121 has passed the engaging members 115, the latter spring back into their original position. The spring-elastic arrangement is achieved by the stays 118 and/or the guiding members 111 and/or their arrangement on the base 119.

Figure 2A:
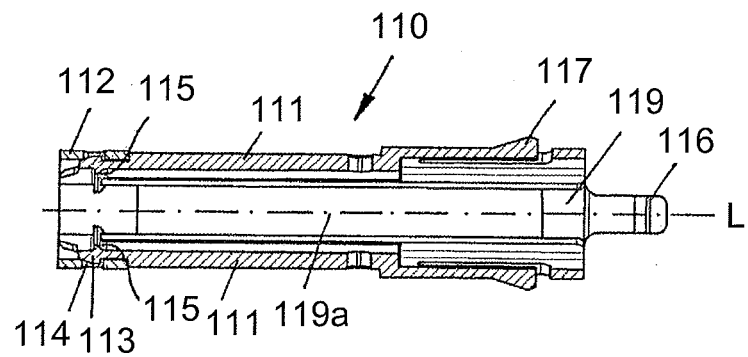
FIG. 2a is a sectional representation of the product container holder from FIG. 1a, with the securing element in a securing position.
Figure 2B:
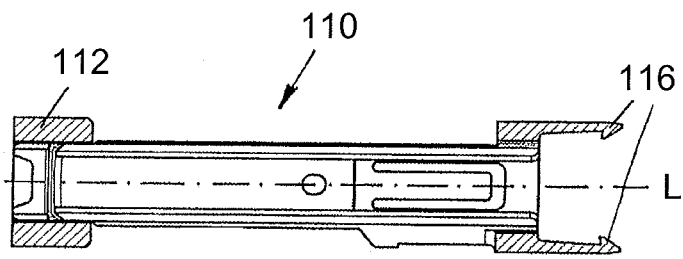
FIG. 2b depicts the product container holder from FIG. 2a, in a sectional representation rotated by 90° about the longitudinal axis.
Figure 2C:
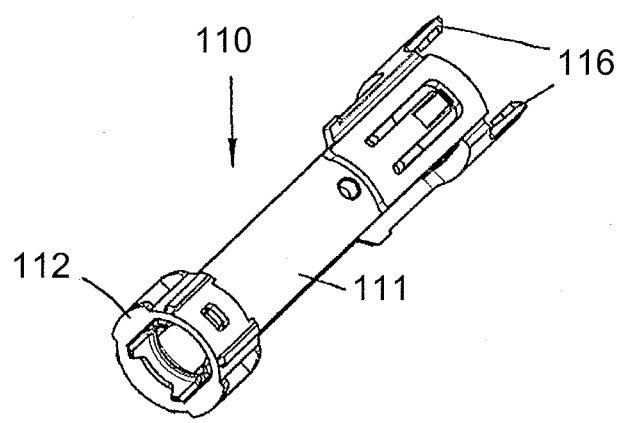
FIG. 2c depicts the product container holder from FIG. 2a, in a three-dimensional view.

FIGS. 2a, 2b and 2c show the product container holder 110 from FIGS. 1a, 1b and 1c, but with a securing means 112 which has been shifted into the securing position. As can be seen from FIG. 2a, the cam 113 has latched into the cavity 114 of the securing means 112. Because the securing means 112 is relatively inflexible and/or rigid, it holds the engaging members 115 in a position in which they are in engagement with the product container 120. The securing means 112 thus prevents the engaging members 115 from moving outward and/or away from the longitudinal axis L. The movement of the engaging members 115 is thus restricted.

Figure 3:
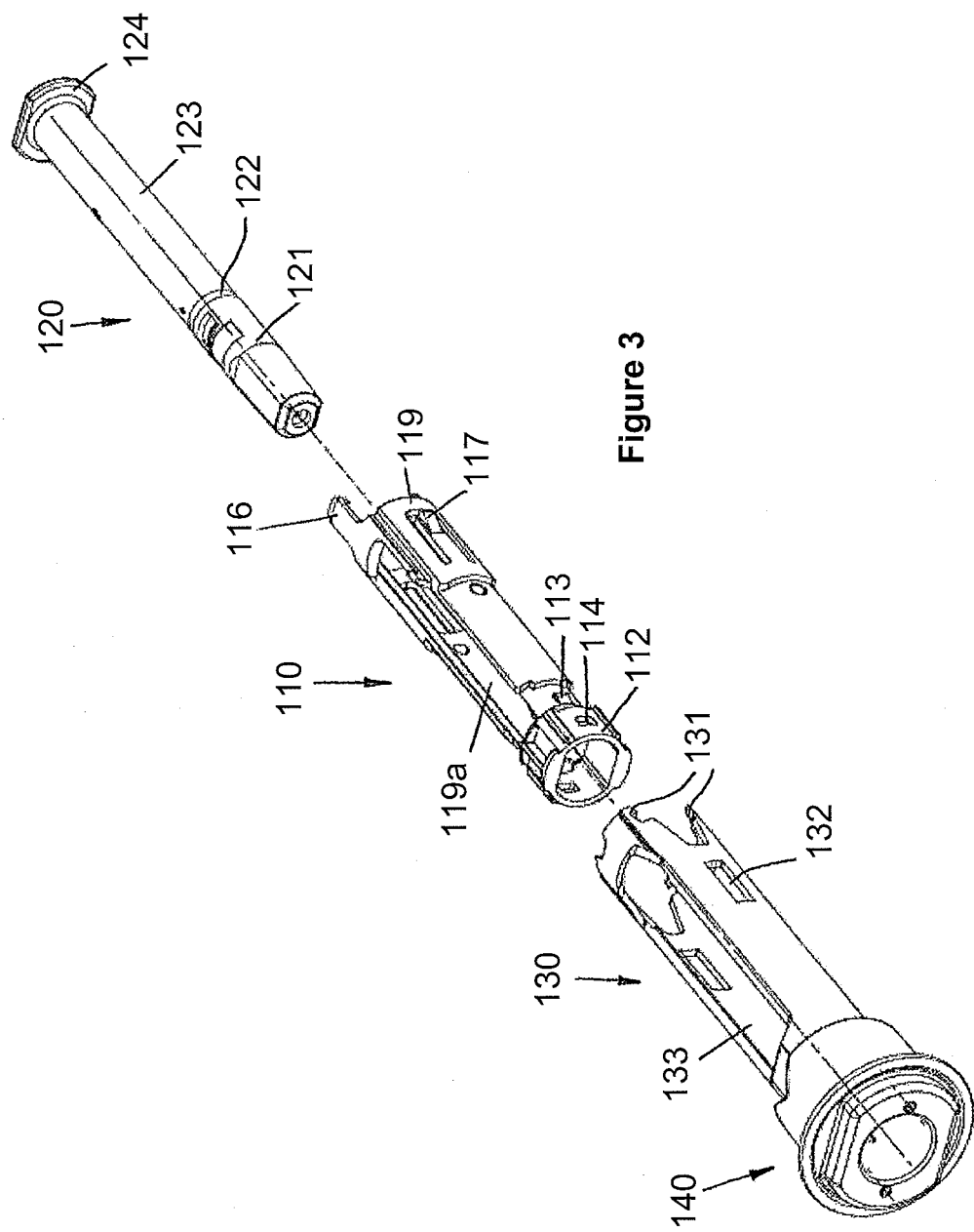
FIG. 3 is an exploded representation of the product container holder from FIG. 1a, together with an embodiment of a product container and a first sub-assembly.

FIG. 3 shows an exploded representation of the product container holder 110 together with a product container 120 and a first sub-assembly which is formed from a front or activating sleeve 130 and a removal cap 140 fastened to it. The representation is suitable for showing how the product container holder 110 and the product container 120 can be integrated into the first sub-assembly (which may be referred to and/or thought of as comprising parts 130, 140).

In a first option (which is not depicted, but which could be based on this description), the product container 120 is first inserted into the product container holder 110 until the engaging members 115 engage with the collar 122 once the needle protecting cap 121 has passed the engaging members 115. A force is then exerted between the lock or securing means 112 and the remaining product container holder 110, such that the stays 118—which serve as a predetermined breaking point—break. This enables the securing means 112 and the rest of the product container holder 110 to move relative to each other, such that the securing means 112 is shifted into the securing position and axially fixed in said position. The combination of the product container holder 110 and the product container 120 is then inserted into the first sub-assembly 130, 140 via the proximal end of the activating sleeve 130. Lastly, the sub-assembly thus formed is inserted into an injection device via the distal end of the injection device, wherein the hooks 116 are latched together with a functional sleeve and the connecting means 131 are latched together with a switching sleeve, as disclosed in DE 10 2007 013 836 A1 (and its equivalent US Publication 2010/0137801).

In another assembly option, the product container holder 110 is first inserted into the sub-assembly, followed by the product container 120 which is inserted until the engaging members 115 engage with the collar 122. This situation is shown in FIGS. 4a and 4b. The cap 140 comprises a support surface 142 on which the distal end of the securing means 112 is axially supported. Applying a sufficiently large force to the proximal end of the product container 120 and/or the product container holder 110 breaks the stays 118 which serve as predetermined breaking points, such that the product container holder 110 and the product container 120 are axially moved together relative to the securing means 112 until the cams 113 engage with the cavities 114, as shown in FIGS. 5a and 5b.

Figure 5A:
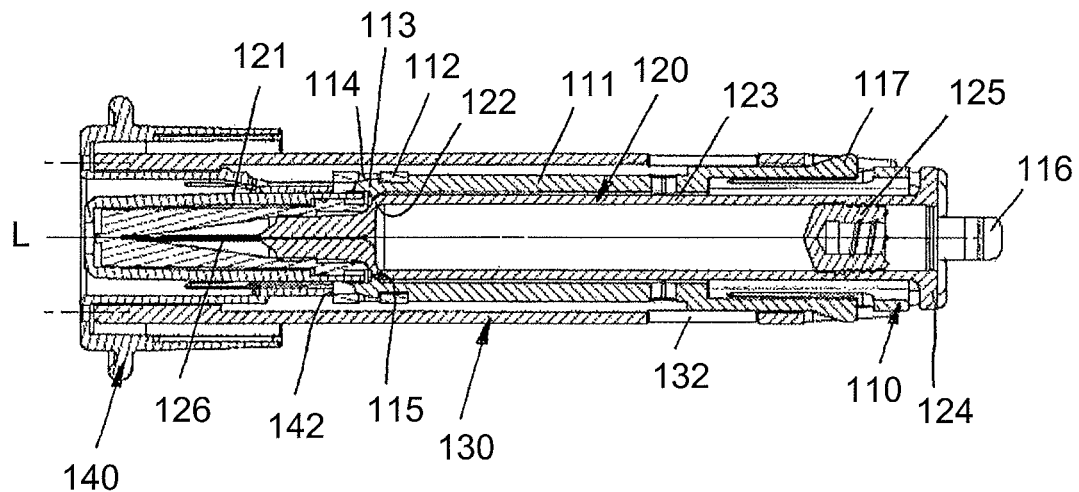
FIG. 5a depicts the combined parts from FIG. 4a in a sectional representation and with the securing member in its securing position.
Figure 5B:
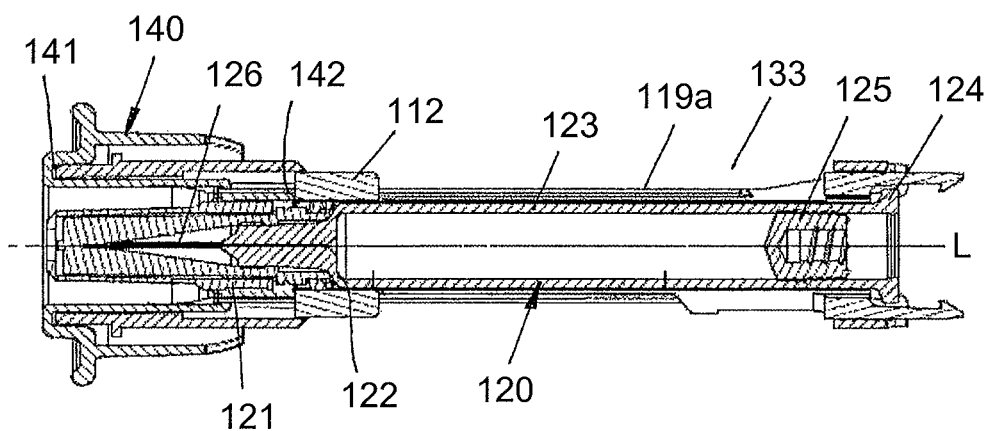
FIG. 5b depicts the combined parts from FIG. 5a, in a sectional representation rotated by 90° about the longitudinal axis.

As can be seen from FIG. 5a, the flange does not lie on the proximal end of the product container holder 110 after assembling. It is thus possible to prevent the flange 124 from breaking when the injection device is triggered.

Before the injection device is triggered, the removal cap 140 is removed in the distal direction. The removal cap 140 engages with the needle protecting cap 121 via an engaging element and slaves it in the removal movement, such that the removal cap 140 can be removed together with the needle protecting cap 121. The product container holder 110 and the product container 120 are not removed along with them, because the product container holder 110 is axially fastened fixedly to the mechanism of the injection device by the fastening members 116, wherein said mechanism for its part diverts the force into the housing, as described in DE 10 2007 013 836 A1 (and its equivalent US Publication 2010/0137801).

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A product container holder for accommodating a product container and a needle protecting sleeve on the product container, wherein the product container holder can be separately handled, said product container holder comprising:
   a) an engaging member for engaging the product container, said engaging member arranged such that it can be moved transversely relative to the longitudinal axis of the product container holder and such that it can block a movement of the product container relative to the product container holder in the distal direction, wherein the engaging member comprises an inwardly protruding cam; and
   b) a securing means which can be moved relative to the engaging member from an initial position into a securing position in which it secures the engagement of the engaging member and product container by restricting the mobility of the engaging member, wherein the securing means is either substantially inflexible or rigid and holds the engaging member in engagement with the product container and wherein the product container holder and the securing means are molded and provided as one piece; wherein
   c) the product container holder can be inserted into an automatic injection device and a product in the product container is administered automatically after the automatic injection device is triggered.

2. The product container holder according to claim 1, wherein the engaging member can be moved flexibly or spring-elastically.

3. The product container holder according to claim 1, further comprising at least one guiding member which can laterally guide the product container, wherein the at least one guiding member is elastically pliable and wherein the engaging member is arranged on the at least one guiding member.

4. The product container holder according to claim 3, wherein a number of guiding members are circumferently provided and connected to each other at their proximal ends and to the securing means at their distal ends.

5. The product container holder according to claim 4, wherein the securing means can block the transverse movement of the engaging member to and away from the longitudinal axis of the product container holder.

6. The product container holder according to claim 1, wherein the securing means surrounds the engaging member and forms a passage for the engaging member and/or the product container and/or is substantially inflexible.

7. The product container holder according to claim 1, wherein in the securing position, the securing means is arranged by a connecting means such that it cannot be axially shifted relative to the engaging member, wherein the connecting means is based on a positive fit and/or force fit.

8. The product container holder according to claim 7, wherein the connecting means, as measured along the longitudinal axis, is attached in the region of the engaging member.

9. The product container holder according to claim 1, wherein the product container holder exhibits an overall length greater in the initial position of the securing means than in the securing position of the securing means, and wherein the securing means forms the distal end of the product container holder in its initial position.

10. The product container holder according to claim 3, wherein the securing means is formed in a force fit, positive fit or material fit on the product container holder, on the at least one guiding member, and in its initial position is arranged in relation to the engaging member such that the engaging member can be moved.

11. The product container holder according to claim 1, wherein the securing means is fastened to the product container holder via at least one stay, wherein the stay serves as a predetermined breaking point and can be broken as the securing means moves into the securing position.

* * * * *